US009610304B2

(12) United States Patent
Marchosky

(10) Patent No.: US 9,610,304 B2
(45) Date of Patent: *Apr. 4, 2017

(54) BONE PASTE COMPOSITION

(71) Applicant: Marfly 2, LP, St. Louis, MO (US)

(72) Inventor: Jose Alexander Marchosky, St. Louis, MO (US)

(73) Assignee: Marfly 2, LP, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/926,444

(22) Filed: Jun. 25, 2013

(65) Prior Publication Data

US 2014/0072638 A1 Mar. 13, 2014

Related U.S. Application Data

(63) Continuation of application No. 12/401,320, filed on Mar. 10, 2009, now Pat. No. 8,470,369.

(60) Provisional application No. 61/035,141, filed on Mar. 10, 2008.

(51) Int. Cl.
| | |
|---|---|
| A61K 38/18 | (2006.01) |
| A61K 35/32 | (2015.01) |
| A61L 27/20 | (2006.01) |
| A61L 27/22 | (2006.01) |
| A61L 27/36 | (2006.01) |
| A61L 27/54 | (2006.01) |
| A61K 45/06 | (2006.01) |

(52) U.S. Cl.
CPC .......... *A61K 35/32* (2013.01); *A61K 38/1816* (2013.01); *A61K 38/1866* (2013.01); *A61K 45/06* (2013.01); *A61L 27/20* (2013.01); *A61L 27/227* (2013.01); *A61L 27/3608* (2013.01); *A61L 27/54* (2013.01)

(58) Field of Classification Search
None
See application file for complete search history.

(56) References Cited

U.S. PATENT DOCUMENTS

| | | |
|---|---|---|
| 5,563,124 A | 10/1996 | Damien et al. |
| 5,711,957 A | 1/1998 | Patat et al. |
| 5,755,792 A | 5/1998 | Brekke |
| 5,830,493 A | 11/1998 | Yokota et al. |
| 5,837,258 A | 11/1998 | Grotendorst |
| 6,372,257 B1 | 4/2002 | Marchosky |
| 2003/0147860 A1 | 8/2003 | Marchosky |
| 2004/0142465 A1 | 7/2004 | Radice et al. |
| 2005/0142163 A1 | 6/2005 | Hunter et al. |
| 2005/0255545 A1 | 11/2005 | Smith |
| 2007/0254040 A1 | 11/2007 | Scaffidi |
| 2008/0031850 A1* | 2/2008 | Bader .................... 424/85.2 |

FOREIGN PATENT DOCUMENTS

| | | | | |
|---|---|---|---|---|
| WO | WO 2005/063965 | * | 6/2005 | ............. A61K 38/18 |
| WO | WO 2007/038009 | * | 5/2007 | ............. A61B 17/58 |

OTHER PUBLICATIONS

Holstein et al, Life Sciences, 2007, vol. 80, p. 893-900.*
Juan et al, European Cells and Materials, 2008, vol. 16, supplement 2, pp. 14.*
Abe, Masamitsu et al., "Model-based Surgical Planning and Simulation of Cranial Base Surgery," Neurol Med Chir (Tokyo) 38, pp. 746-751, 1998.
Bodmeier, Roland et al., "Preparation and Evaluation of Drug-Containing Chitosan Beads," Drug Development and Industrial Pharmacy, 15(9), 1475-1494 (1989).
Chandy, Thomas et al., "Chitosan—As a Biomaterial," Biomat., Art. Cells, Art. Org., 18(1), 1-24 (1990).
Gaserod, Olav et al., "Microcapsules of alginate-chitosan—I A quantitative study of the interaction between alginate and chitosan,"Biomaterials 19 (1998) pp. 1815-1825.
ISR dated Apr. 29, 2009 regarding PCT/US09/36673, two pages.
Jameela, S.R. et al., "Glutaraldehyde cross-linked chitosan microspheres as a long acting biodegradable drug delivery vehicle: studies on the in vitro release of mitoxantrone and in vivo degradation of microspheres in rat muscle," Biomaterials 16, No. 10, (1995) pp. 759-775.
Katz, D.M. et al., "Quantification of holographic fringe data: comparison of intact and implanted femurs," Medical Engineering & Physics 20 (1998) 114-123.
Kibblewhite, Douglas J., "Transforming Growth Factor-B Accelerates Osteoinduction in a Craniofacial Onlay Model," Growth Factors, 1993, vol. 9, pp. 185-193.
Ko, Kathryn, "Superimposed holographic impage-guided neurosurgery," J Neurosurg 88:777-781, 1998.
Miyazaki, Shozo et al., "Thermally reversible xyloglucan gels as vehicles for rectal drug delivery," Journal of Controlled Release 56 (1998) 75-83.
Phillips et al., "Do growth factors stimulate angiogenesis? a comparison of putative angiogenesis factors," Wounds; a compendium of clinical research and practice; vol. 9, No. 1, 1997, pp. 1-14.
Rao, S. Bhaskara et al., "Use of chitosan as a biomaterial: Studies on its safety and hemostatic potential," Journal of Biomedical Materils Research, vol. 34, 21-28 (1997).
Solheim, E., "Osteoinduction by demineralised bone," International Orthopaedics (SICOT) (1998) 22:335-342.
Tabata, Yasuhiko et al., "Bone regeneration by fibroblast growth factor complexed with biodegradable hydrogels," Biomaterials 19 (1998) 807-815.

(Continued)

*Primary Examiner* — Allison Fox
(74) *Attorney, Agent, or Firm* — Woodard, Emhardt, Moriarty, McNett & Henry LLP

(57) ABSTRACT

Bone paste compositions are described, which promote bone healing and remodeling by stimulating bone marrow elements using a combination of hemopoietic agents, angiogenic agents and a bone molecular signaling material.

17 Claims, No Drawings

(56) References Cited

OTHER PUBLICATIONS

Thomson, Robert C. et al., "Fabrication of biodegradable polymer scaffolds to engineer trabecular bone," J. Biomater. Sci. Polymer Edn, vol. 7, No. 1, pp. 23-38 (1995).

Zentner, Andrej et al., "A holographic study of variations in bone deformations resulting from different headgear forces in a macerated human skull," The Angle Orthodontist, vol. 66, No. 6, 1996, pp. 463-472.

* cited by examiner

BONE PASTE COMPOSITION

CROSS REFERENCE TO RELATED APPLICATIONS

This application is a continuation of U.S. patent application Ser. No. 12/401,320, filed Mar. 10, 2009, pending, which claims the benefit of U.S. Provisional Patent Application No. 61/035,141, filed Mar. 10, 2008, entitled BONE PASTE COMPOSITION, each of which is herein incorporated by reference in its entirety.

GOVERNMENTAL RIGHTS

Not applicable.

INCORPORATION-BY-REFERENCE OF MATERIAL SUBMITTED ON A COMPACT DISC

Not applicable.

BACKGROUND OF THE INVENTION

The present teachings relate generally to methods and compositions for promoting repair and growth of bone, and more particularly to methods for treating osteoporosis and other bone conditions.

Osteoporosis remains a disease or condition characterized by the progressive loss of bone substance, density and strength. In addition and concomitant with the loss of bone tissue, there is a loss of hemopoietic tissue from the marrow of blood elements producing bones. The blood elements comprise red blood cells, white blood cells, platelets, the precursor cells of these cells and other cells common to the bone marrow. Whether the loss of the hemopoietic tissue is the result of mechanical loss of bone matrix or is biologically, hormonally, or biochemically mediated is inconclusive at the present time. Various bone diseases, injuries, or surgical interventions in humans and other vertebrates result in bone defects or fractures. Bone growth or restitution is often desired to alleviate these conditions. The bone growth may be desired in areas where bone previously existed and is partially or completely absent, or where its continuity has been disrupted. Situations where such regeneration of bone is necessary or desirable include the healing of fractures, prevention of fractures, or increasing the bone mass in osteoporotic bones.

Certain compositions to encourage bone growth are known and are available commercially, for example as Grafton® (Osteotech, Eatontown, N.J.). These compositions consist of a porous solid, semisolid, paste or gel material including materials such as gelatin, hyaluronic acid, collagen, amylopectin, demineralized bone matrix, and/or calcium carbonate. However, none of these compositions are directed at regenerating the hemopoietic elements of the marrow nor do they incorporate agents for stimulating hemapoiesis and angiogenesis.

BRIEF SUMMARY OF THE INVENTION

In one aspect, the present teachings provide a composition comprising at least one hemopoietic agent, at least one angiogenic agent, a bone molecular signaling material, a scaffolding material comprising cancellous bone and a gel component.

In another aspect, the present teachings provide a bone paste composition comprising one or more hemopoietic agents selected from the group consisting of: erythropoietin, erythropoietin growth factors, and hemopoietic factors, which are present in an amount from 10 to 50,000 U or 3% or less by volume of the composition, one or more angiogenic agents selected from the group consisting of chitosan components of medium to high molecular weight, and hyaluronic acid components (which can comprise a mixture of sulfated and non-sulfated hyaluronic acid components), a bone molecular signaling material comprising demineralized bone matrix and non-decalcified bone matrix optionally in combination with hyaluronic acid, wherein the demineralized bone matrix is present at 5-50% by volume of the composition, and the non-decalcified bone matrix is present at 5-50% by volume of the composition, wherein when present the hyaluronic acid is present at 5-20% by volume of the composition, a scaffolding material comprising cancellous bone, wherein the cancellous bone is milled to 0.1-1.5 mm in its longest diameter and is present at 10-50% by volume of the composition, and a gel material comprising a 0.5-25% (w/v) concentration of a compound selected from the group consisting of chitosans, alginates, hyaluronic acids, heparans, and any combination thereof.

In another aspect, the present teachings provide a composition comprising at least one hemopoietic agent encapsulated in a carrier comprising at least one of a chitin, chitosan, alginate, heparan, and a hyaluronan, the carrier configured to provide continuous and slow release of the hemopoietic agent, at least one angiogenic agent, a bone molecular signaling material comprising demineralized bone matrix present at 5-50% by volume of the composition, non-decalcified bone matrix present at 5-50% of the composition, and optionally hyaluronic acid, a scaffolding material comprising cancellous bone, wherein the cancellous bone is milled to 0.1-1.5 mm in its longest diameter and is present at 10-50% of the composition, and a gel component comprising a 0.5-25% (w/v) concentration of a material selected from the group consisting of chitin, chitosan, alginate, heparans, hyaluronic acid, a combination of alginate and chitosan, and a combination of hyaluronic acid and chitosan, the gel component present at 10-80% by volume of the composition.

In another aspect, the present teachings provide a bone paste composition comprising by volume percent of the composition, 1% or less of one or more hemopoietic agents, 2% or less of one or more angiogenic agents, 70% or less of a scaffolding material, 40% or less of a bone molecular signaling material, and 20% or less of a gel material.

DETAILED DESCRIPTION OF THE INVENTION

As used herein, the term "cancellous bone" refers to the medullary portion of bone, devoid of hematogenous and other cellular material, and typically derived from human or animal tissues or cadavers.

The terms "hemopoietic", "hematopoietic", "hematogenous", or "erythropoietic" are used herein to refer to the that characteristic of tissues that are composed of and/or produce blood components and blood precursors such as red blood cells, white blood cells, platelets, such tissues typically being found in the interstices of cancellous bone.

The terms "hemopoietic factors" "hematopoietic factors", "hematogenous factors", and "erythropoietic factors" as used herein refer to substances capable of inducing and/or stimulating the formation of hemopoietic, hematopoietic, hematogenous, or erythropoietic tissue.

The term "hemopoietically effective" as used herein refers to an amount of a substance that produces one or more of the following clinical effects: increased hematocrit, stimulation of hemoglobin, increased stimulation of reticulocyte response, development of ferrokinetic activity, and erythrocyte mass changes, and encompasses an amount of a substance that may in the alternative be referred to as any of "hematopoietically effective", "hematogenously effective", and "erythropoietically effective".

The term "hemopoietic agent" refers to a substance that when administered to biologic tissue or to an organism produces one or more of the following effects: increased stimulation of hemapoiesis, increased hematocrit, stimulation of hemoglobin, increased stimulation of reticulocyte response, development of ferrokinetic activity, and erythrocyte mass changes. The term "hemopoietic agent" as used herein is intended to encompass any material that may in the alternative be referred to as any of "hematopoietic agent", "hematogenous agent", or "erythropoietic agent".

"Angiogenic material" refers to substances that produce neovascular growth and invasion of implants to supply circulatory needs. Inclusively, but not exclusively amongst these substances are chitosans, hyaluronics, heparans, alginates, angiogenins, vascular endothelial growth factors, fibroblast growth factors, platelet derived growth factors, tissue growth factors, erythropoietic factors, and others.

The term "demineralized bone matrix" ("DBM") as used herein refers to ground cortical or cancellous bone that has been demineralized. Up to 8% of the original mineral content may still exist within this definition. Demineralization is achieved for example by treating the ground bone with acid, usually 0.6N hydrochloric acid. The cortical bone may be obtained from any source, including human or animal cadavers. DBM is known to contain osteoinductive growth factors.

The term "non-decalcified bone matrix" ("NBM") as used herein refers to ground cortical bone which has not been demineralized. NBM is known to contain osteoinductive growth factors.

The term "osteoconductive" as used herein refers to materials that provide an environment for ingrowth and orientation of osteogenic cells from surrounding tissues. Such materials are generally porous materials, i.e., providing latticework structures similar to cancellous bone.

The term "osteogenic" as used herein refers to the process of forming new bone. This formation requires signaling, modulating, and transforming molecules.

The term "osteoinductive" as used herein refers to the ability of a material to induce the production of osteoblasts from precursor cells, in particular mesenchymal stem cells. The osteoinductive material may act directly as a growth factor that interacts with precursor cells to induce the osteoblastic differentiation, or the material may act indirectly by inducing the production of osteoinductive growth factors. This induction also requires signaling, modulating, and transforming molecules.

When used herein, the term "biocompatible" refers to materials which, when incorporated into the composition, have low toxicity, acceptable foreign body reactions in the living body, and affinity with living tissues.

The term "bone molecular signaling material" as used herein refers to a material having the ability to induce the production of osteoblasts from precursor cells, in particular mesenchymal stem cells. The osteoinductive material may act directly as a growth factor that interacts with precursor cells to induce the osteoblastic differentiation, or the material may act indirectly by inducing the production of osteoinductive growth factors. This induction also requires signaling, modulating, and transforming molecules.

The term "chitin" as used herein refers to poly(1,4)2-amino-2-deoxy-β-D-glucan, which is a biologically abundant polysaccharide that forms, e.g., the structural component of the cell walls of many fungi and the shells of insects and shellfish. The level of acetylation may be above 50%.

The term "chitosan" as used herein refers to N-deacetylated chitin. Deacetylation is generally accomplished by treatment of chitin with alkali such as sodium hydroxide. The degree of N-deacetylation can be controlled by controlling the amount of alkali treatment and time of exposure. The length of the chitosan polysaccharides can also be decreased by degrading the high molecular weight molecule with, e.g., 1 N hydrochloric acid, or by enzymatic treatment. Chitosan in acidic solutions forms gels at concentrations as low as 1% (w/w in 1% v/v acetic acid) (Bodmeier et al., 1989, Drug Devel. & Ind. Pharmacy 15:1475) and is insoluble at pH>6.5. Chitin and chitosans can be cross-linked with charged radicals (i.e. glutaraldehyde, carbodiimide, lysine, vinyl, etc.) to obtain strongly bonded polymers that can be formed into solid or tubular structures. For information on various other characteristics and useful manipulations of chitosan, see, e.g., PCT patent publication WO 98/22114, the disclosure of which is herein incorporated by reference.

No particular form of chitin or chitosan is to be regarded as necessarily more useful than any other form for use in the present invention.

As used herein the term "alginate" refers to a copolymer of (1,4)-α-L-guluronic acid and β-D-mannuronic acid produced by brown algae. A gel is formed when a 2% alginate solution interacts with divalent cations such as calcium. See Gåserød O, Smidsrød O, Skjåk-Braek G., 1998, Biomaterials 19(20):1815-25 for additional information on characteristics of alginate.

As used interchangeably herein the terms "hyaluronic acid" and "HA" refer to a copolymer of glycosoaminoglycans ("GAG") of variable chain lengths and molecular weights.

As used herein the term "hyaluronans" refers inclusively to the organic and the inorganic salts of glycosoaminoglycans that act as important regulators of angiogenesis and in particular of the growth and migration of vascular endothelial cells.

Heparans refers to any of the many varieties of the heparin molecules.

The term "1 to n", when used with the name of a growth factor, means that various forms of the growth factor, both known and not yet discovered, are intended to be included.

Unless otherwise indicated, all percentages referring to relative contributions of the various elements of the compositions refer to percent by volume of the total volume of the composition.

The contents of each of the references cited herein are herein incorporated by reference in their entirety.

The invention is based in part on the surprising discovery that stimulation of bone marrow elements promotes bone healing and further that combinations of chitosan with bone molecular signaling material such as demineralized bone matrix and/or ground or chipped cancellous bone are especially well-suited to achieving full hematogenous and bone tissue formation and growth in a vertebrate. These compositions and methods are particularly useful for stimulating hematogenous and bone formation in humans and other mammals, especially when bone repair is needed. For example, the compositions and methods are especially useful in repairing bones following bone trauma or bones that have degenerated due to a disease process or to aging.

The compositions are formulated utilizing the previously unappreciated finding that hemopoiesis is a pivotal and crucial factor for inducing bone formation and growth. This is a surprising and unexpected finding because bone (as opposed to marrow) is hypo-vascular. Thus, hemopoiesis stimulating factors are not expected to have an effect on bone formation and growth. While certain angiogenesis stimulating factors (including compounds such as chitosans, hyaluronic acid, hyaluronans, chitin, alginates, erythropoietic hormones or factors, vascular endothelial growth factors, platelet derived endothelial cell growth factors, basic fibroblast growth factors, and interleukin-8, and other materials known to stimulate the production of angiogenesis stimulating factors (e.g., chitosan), have been considered as helpful components of a material for filling in damaged or degenerate bone, the compositions and methods disclosed herein surprisingly improve bone formation over that obtained using the known bone repair compositions, including those that include only angiogenic agents. Put another way, the compositions as disclosed herein promote bone production by invoking the activity of tissues in the interstices of the cancellous portion of bone, which the inventor has determined can be stimulated with a combination of angiogenic agents and hematopoietic agents to further promote bone regrowth in part by generating hematogenous tissue.

The compositions of the invention thus are composed of at least a hemopoietic agent, an angiogenic agent (i.e. an angiogenesis-stimulating agent), a bone molecular signaling material, a scaffolding component, and a carrier substance such as for example a gel or gel-like substance. The hemopoietic agent or agents are present at 5% or less by volume of the total composition, and preferably are present, for example, at 3% or less by volume of the composition, at 2% or less by volume of the composition, at 1% or less by volume of the composition, or 0.5% by volume of the composition. Alternatively, a hemopoietic agent or a combination of hemopoietic agents is added in amount totaling from 10 to 50,000 Units. The carrier substance provides for easy flow and volumetric conformation of the composition, holds together the remaining components, allows the slow release of the remaining components, and also prevents the composition as a whole from migrating from an implant site.

It is to be noted that certain materials that may be used in the compositions of the present invention may serve as more than one of the above components. Also, the compositions optionally include additional cofactors or elements that contribute bone healing and remodeling, and may include elements yet unrecognized that promote bone healing and remodeling through mechanisms yet unknown.

When a composition of the present invention is placed in a location where bone formation and/or growth is desired, for example at a site of bone degeneration or injury, the components of the composition work together to achieve the desired purpose of bone repair and healing. The angiogenic agent stimulates the growth of neovasculature from existing host tissue, which is vital for the process of new bone formation. The bone signaling material is an osteoinductive component that induces the formation of bone-forming osteoblasts from precursor cells, in particular mesenchymal cells. The hemopoietic agent stimulates the formation of blood precursors and cells, which may, in a feedback loop further stimulate the angiogenic and osteogenic functions.

The carrier material, e.g. a biocompatible gel, holds the remaining components and allows slow release thereof to provide release of these components to the local environment over a period of time corresponding to a substantial portion of the entire bone forming and regrowth process. The selection of material for each component, and the relative contributions of particular components to the composition, and particularly the choice and relative amount of carrier material can be varied to adjust the properties of the final composition in accordance with an intended use. For example, the carrier material can be selected from more fluid biocompatible gels, to impart the characteristic of easy flow, and thus permitting the composition to volumetrically fill the targeted tissue space and to conform to the local site to deliver the growth factors to a site of action. A more fluid composition may be preferred, for example, when a relatively small, narrow or inaccessible tissue space is the target repair site. This filling action also serves to interfere with the ingrowth of fibrous scar-forming tissue and other tissues which could create defects, voids, etc. that may interfere with proper bone formation, as any bone that does form around such ingrown tissue may be weak, permitting fractures and failures. In other applications, a less fluid and more paste-like composition may be preferred, for example to pack a large defect in a long bone. In such applications, a less fluid gel may be selected as the carrier material, or an alternative carrier material may be selected. The carrier material may vary in viscosity or density as may be determined to adapt the consistency of the composition to the target tissue. In situations in which an open operation allows wide exposure of the target area, a more dense composition, such as putty or a moldable gel, will be useful and can be pressed or molded into the site without difficulty. For example, a bone fracture that is being repaired by open exposure would be ideal for putty consistency. However, if the target is a narrow recess being approached percutaneously with a narrow needle, a less viscous or less dense overall composition is preferred. Accordingly, the concentration of the remaining, active agents may be reduced in order to achieve the desired consistency. For example, when the intended use is to inject the composition into a vertebra, it may be preferred to use a larger gauge needle (e.g. an 8 gauge needle) and therefore the composition can be relatively viscous though much less so than a composition having a putty-like consistency. Alternatively, the intended use may involve injection of the composition into a posterior articulation of the spine, which is a narrow recess that would require a smaller, e.g. 25-gauge needle, to achieve access. For such a procedure a relatively more dilute, less viscous composition is preferred in order to achieve adequate flow.

Any known hemopoietic agent and any known angiogenic agent are useful in the compositions of the present invention. Non-limiting examples of suitable angiogenic agents are individual growth factors known to induce angiogenesis such as hyaluronic acid, hyaluronan, hyaluronan derivatives or complexes; alginates or alginate derivatives or complexes; chitin, chitosan, a derivative of chitin or of chitosan, erythropoietin, endothelial growth factors, fibroblast growth factors, and angiogenic factors, and any combination thereof.

Non-limiting examples of suitable hemopoietic agents include erythropoietin, erythropoietin growth factors, hemopoietic-stimulating hormones, hemopoietic factors, hematopoietic-stimulating substances, heparin and heparans, dermatans, dextrans, or any combination thereof, and other factors with comparable hemopoietic activity as may be routinely determined according to bioassays known in the art.

Because of the different molecular lengths and weights, characteristics and functions of chitosans and its complexes and derivatives, hyaluronic acids, hyaluronan and its complexes and derivatives, alginates and its derivatives and complexes, the precise quantities of each such component, i.e. the relative amount of a particular such substance in the present compositions, can be varied according to principles known to those of skill in the art to achieve desired characteristics of the composition, such as in particular flowability or resulting hardness of implants.

The angiogenic nature of a material used as an angiogenic agent can be established or confirmed by various assays known in the art, including for example the incorporation of the material into a slow release polymer and implanting the polymer into a rabbit cornea (Phillips et al., 1997, Wounds 9:1). Similarly, the hemopoietic activity of a material can be determined by well-known assays of hemopoietic or erythropoietic activity, such as but not limited to measurement of hematocrit.

Osteoinductive compounds useful in the compositions of the invention include purified materials known to have these characteristics. Such materials alone or in various combinations may include bone morphogenic proteins (1 to n), transforming growth factors (TGF)(1 to n), insulin growth factors (IGF)(1 to n), platelet derived growth factors (PD-GF), fibroblast growth factors (FGF)(1 to n), tumor necrosis factor (TNF), interleukins (IL)(1 to n), various cytokines, and vitamins such as vitamin D (1 to n).

Chitosan has also been shown to promote the differentiation of mesenchymal stem cells into osteoblasts (Klokkevold et al. 1996 J. Periodontology 67:1170), and may thus serve to stimulate at least a part of the mesenchymal-osteoblast differentiation process.

Certain complex materials can also conveniently serve as sources of osteoinductive molecules, and such materials and combinations thereof serve as a bone or molecular signaling material. Osteoconductive molecules are known to be provided by demineralized bone matrix ("DBM"), which is prepared by grinding cortical bone tissues (generally to 100-500 μm sieved particle size), then treating the ground tissues with hydrochloric acid (generally 0.5 to 1 N). See, e.g., Solheim, 1998, Int. Orthop. 22:335-42. DBM is commercially available, e.g., Grafton® (Osteotech, Eatontown, N.J.); Dynagraft® (GenSci, Irvine, Calif.). It is believed, however, that the acid treatment process used in preparing DBM denatures and/or solubilizes some of the osteogenic molecules present in untreated bone, destroying the osteogenic nature of the denatured molecules or allowing them to leach out of the DBM preparation. Therefore, a preferred source of osteoinductive molecules is non-decalcified bone matrix ("NBM"), which is ground cortical bone tissues that are not acid-treated. A combination of NBM and DBM is also useful in the compositions as a source of osteoinductive molecules. The addition of hyaluronic acid may further enhance the osteoinductivity of the mixtures. Alternatively, a combination of hyaluronates and chitosan and derivatives thereof has suitably osteoinductive qualities to be used as a bone molecular signaling material, or such a combination may be used in combination with a combination of NBM and DBM.

The osteoinductive nature of a compound may be determined by known methods such as histomorphometric analysis of trabecular bone formation around a rabbit cranial periosteum implant comprising the putative osteoinductive compound in DBM. See, e.g., Kibblewhite et al., 1993, Growth Factors 9:185.

As used herein, the term "bone molecular signaling material" is an osteoinductive material that may include for example a combination of DBM and NBM. Typically DBM is present at an amount of from 5% to 50% by volume of the composition, and NBM is present at an amount of from 5% to 50% by volume of the composition. Use of DBM and NBM together as the bone molecular signaling material is a preferred embodiment and based in part on the observation that fusions performed with structural allograft (NMB; without or with added DBM) heal better than fusions utilizing DBM alone. When a combination of DBM and NBM is used, any ratio of DBM:NBM (by volume) can be used, including for example 10:1, 9:1, 8:1, 7:1, 6:1, 5:1, 4:1, 3:1, 2:1, 1:1, 1:2, 1:3, 1;4, 1:5, 1:6, 1:7, 1:8, 1:9, and 1:10. When a combination of DBM and NBM is used, hyaluronic acid is optionally included in the combination forming the bone molecular signaling material, in an amount equal to 5 to 30% by volume of the composition.

Any one or more of the components of the composition can be prepared as a suspension of carrier structures such as vesicles, micelles or cysts that are composed of an encapsulating material (i.e. materials that encapsulate the component within a vesicle, micelle or cyst). For example, to prepare a component encapsulated in vesicles, cysts or micelles, one method is to drip very small drops of the desired component(s) into a bath containing the encapsulating carrier(s) that will form the envelope of the vesicle, cyst or micelle, under controlled pH, temperature and carrier(s) concentration. This method allows a range amount of the desired component to be incorporated into the carrier structures. Other methods as known in the art for forming vesicles, micelles or cysts can be used.

The scaffolding material or materials provide direction and a structure for the development of host neovasculature and osteogenic cells. Materials useful for this purpose are known in the art and include for example hydroxyapatite-chitosan and sulfated-chitosan composites, materials such as those disclosed in U.S. Pat. Nos. 5,830,493; 5,563,124; 5,755,792; or 5,711,957, DBM, or, preferably, cancellous bone, chitosan, compositions of chitosans and hyaluronates, alginates and compositions thereof, chitosan-protein fibers, and chitin-protein fibers. Cancellous bone may be obtained from any source, including cadavers. When used as a scaffolding material, the cancellous bone is preferably milled to 0.1-1.5 mm in its longest diameter. In an exemplary embodiment, cancellous bone is used as the scaffolding material. It is not known to provide any live cells. Alternatively, $CaSO_4$, $CaCO_3$, and other calcium salts can also be formed into crystals, either alone or combined with chitosans, hyaluronates or alginates, to be used as scaffolding material.

The scaffolding material is utilized in the compositions at 70% or less but at least 0.1% by volume of the composition. In one embodiment, the scaffolding material is present at 60% or less by volume of the composition, in another embodiment at 50% or less by volume, in another embodiment 40% or less by volume, in another embodiment at 30% or less by volume, and in another embodiment at 20% or less by volume of the composition. In an exemplary embodiment in which cancellous bone is used as the scaffolding material, the cancellous bone is present at 10-50% by volume of the composition. In another exemplary embodiment in which cancellous bone is used as the scaffolding material, the cancellous bone is present at 0.1-30% by volume, and preferably 10% by volume of the composition.

The carrier material that holds the hemopoietic agent, angiogenic agent and bone molecular signaling material and allows the slow release of these components can be any biocompatible compound known to have these properties. The slow release of these factors provides the maximum angiogenic and osteogenic benefit. See, e.g. Tabata et al., 1998, Biomaterials 19:807. Examples of materials useful for this purpose include gelatin hydrogels (Tabata et al.) and alginate or chitosan beads, vesicles or cysts (Gåserød O, Smidsrød O, Skjåk-Braek G., 1998, Biomaterials 19(20): 1815-25) or micelles. As previously discussed, this material, if desired, may also provide a flowable characteristic to the composition. A preferred material that provides these functions is a gel material based on one or more biocompatible molecules, such as a chitosan gel, which may also serve as a material to prevent movement of the composition (see below), is also advantageous inasmuch as it also is an angiogenesis-stimulating agent. The gel material may also include a mixture of biocompatible molecules such as any of those selected from the group consisting of chitin, chitosan, alginate, and hyaluronic acid, including a mixture of alginate with chitosan, or a mixture of hyaluronic acid and chitosan. A chitosan derivative or complex thereof may be used in this regard, including the various chitosans of variable molecular weights and chain lengths. The gel material is present at 5-80% by volume of the composition, as a 0.5-25% (w/v) concentration of a biocompatible molecule in a gelatin base. Within the stated range of 5-80% by volume of the composition, alternative embodiments of the composition incorporate the gel material at no more than 50% by volume of the composition, no more than 30% by volume of the composition, no more than 20% by volume of the composition, and no more than 10% by volume of the composition. Within the stated range of 0.5-25% (w/v), the gel material may be a material incorporating the biocompatible molecule in a gelatin base at at least 20%, or no more than 15%, or no more than 5%, or no more than 3%. Exemplary embodiments of the composition include a gel material having a 1% or a 3% (w/v) concentration of the biocompatible molecule, present at no more than 20%, and preferably no more than 10% by volume of the composition. As will be readily understood, adjustments to the overall consistency of the composition will be made according to its intended purpose (e.g. target tissue site), and such adjustments will be readily made primarily by adjusting the concentration of, and relative amount of the gel material in the overall composition.

Alternatively, the angiogenic agent and/or bone molecular signaling material can be encapsulated in microcapsules dispersed in the composition. The microcapsules can be composed of, e.g., chitosan or a mixture of chitosan and alginate (Gåserød O, Smidsrød O, Skjåk-Braek G., Id.), xyloglucan polysaccharide gel (Miyazaki et al., 1998, J. Controlled Release 56:75), or from components selected from the group comprising hyaluronates, alginates, chitosans, compositions of chitosans and alginates, chitosans and hyaluronic acids, chitosans, alginates and hyaluronates, free floating or further contained in larger vesicles (i.e. vesicles within vesicles) developed from combinations of the same various components or from hydrocarbons and/or from surfactants or from a combination of the various components hereof; or any other biocompatible formulation known in the art. The microcapsules, micelles or beads may be dispersed evenly throughout the composition. Alternatively, the microcapsules can be concentrated in an area of the composition where stimulation of hematopoiesis, angiogenesis or osteogenesis is most useful. An example of such an area is the area adjacent to existing, live bone, where the angiogenesis-stimulating agent would be expected to stimulate the production of neovasculature from the live bone.

The compositions may further comprise a substance for preventing the composition from moving away from the location where it is placed. This substance is preferably a semi-solid, moldable structure to allow the composition to be formed into the shape needed for the particular application to which the composition is being used. Again, this material can also be flowable, angiogenic, osteoconductive, and/or osteoinductive, providing aspects of other components of the compositions. Useful materials for this purpose include chitosans, hyaluronates, alginates, alginate derivatives, gelatins, hydroxyapatite, tricalcium phosphate, calcium carbonate, and other organic and non-organic mineral salts, vitamins, and hyaluronic acids. Preferred gel-forming materials are chitosans and chitosan derivatives such as imidazolyl chitosan or methylpyrrolidinone chitosan, alginates and hyaluronates. Combinations of these materials may also be utilized advantageously to create the consistency needed for any particular application. The component proportions of the materials in these combinations may be modified to adjust, e.g., the pH, or the consistency of the composition.

As previously mentioned, certain materials can provide the function of more than one component of the composition. In particular, the angiogenic/osteogenic slow release component and the component that prevents the composition from moving can be advantageously combined within one material. Hyaluronic acids, hyaluronans or chitosans or chitosan derivatives such as imidazolyl chitosan or methylpyrrolidinone chitosan or alginates may provide such a multi-component function. The percentage of hyaluronic acids, chitosans or alginates is adjusted in these compositions to provide the desired thickness and flow characteristics of the composition, as well as the desired rate of release of the angiogenic and osteogenic growth factors. As previously discussed, hyaluronic acid and/or chitosans can also wholly or in part provide the angiogenic stimulation component of the compositions. In addition, the hemopoietic stimulating agent erythropoietin may stimulate hematogenous/angiogenic/osteoblastic activity.

The thickness of the gels useful for this invention is known to be affected by other materials present in the composition, particularly calcium-containing materials such as tricalcium phosphate, calcium sulfate and calcium chloride. For example, the thickness of chitosan gel is known to be affected by the presence of tricalcium phosphate. See, e.g. U.S. Pat. Nos. 5,563,124; 5,711,957. Also, the thickness of alginate gels is affected by the presence of calcium chloride. Since NBM retains the calcium phosphate from the bone matrix, it provides calcium, which can combine with the chitosan gel to thicken and harden the gel, particularly in an acidic environment. Therefore, the thickness of chitosan gel used in the compositions may be increased by increasing the amount of NBM, or increasing the NBM:DBM ratio, if both materials are used for the bone molecular signaling component.

Chitosan or chitosan derivatives can also be used alone (without DBM or NBM) to stimulate bone growth. In particular the chitosan-based materials can be formed into solid or tubular structures that can be used as supporting, bridging or guiding structures for bone repair. Chitosan or chitosan derived beads or vesicles may be useful in sequestering the hematopoietic agent(s), angiogenic agent(s) and bone molecular signaling materials for delayed release into the tissues to extend the duration of action. Chitosans combined with alginates or with hyaluronans may also serve similar functions.

Chitin-based materials may also provide similar functions. These structures can be made, for example, using the glutaraldehyde cross-linking method disclosed in Jameela et al., 1995, Biomaterials 16:769-775. Similar methods can be employed to make other cross-linked chitin or chitosan materials, e.g., those cross-linked with carbodiimide, lysine, and vinyl. Incorporating fibers of these chitin, chitosan or derivatives in multidirectional woven or layered patterns provides further strength. For example, solutions of these compounds can be conformed into desired shapes, (e.g., sheets, rods, columns, tubes, etc.) and solidified by, e.g., drying, curing with vacuum or heat, or addition of salts of minerals (i.e. calcium, sodium). Porous foam-like chitin or chitosan-based materials with a bone-like structure can also be prepared, e.g. by the method disclosed in Thomson et al., 1995, J. Biomaterials Sci. 7:23-38. These solid materials could also be impregnated with chitosan solutions before or after implantation to fill the structure and add adhesiveness and strength.

The compositions are useful in methods where they are applied to sites in humans or other vertebrates where bone formation and growth is desired. The compositions are useful, for example, at sites with bone defects due to surgery (as occurs, e.g., with the removal of a bone tumor), trauma, or a congenital deficiency (e.g., to correct a cleft palate). Periodontal applications include the use of the compositions to strengthen teeth implants and to repair surgically cut facial bones, e.g., mandibles during plastic surgery.

The compositions may be applied as a coating of an allograft or autograft used to fill in the defect, or at the junction of the graft and the native bone (the graft-host interface). Alternatively, the compositions may be applied as a gel or as a rigid, bonelike structure (e.g., comprising a chitin or a chitosan derivative as previously described), optionally surrounded and/or impregnated with more flowable compositions to fill in undesired gaps. The rigid structure can serve as a bone replacement, providing strength and support until new bone replaces the structure. These rigid structures can, for example, serve as a bone strut, taking the shape of honeycombed tubular or flat structures. The rigid structures can also be formed into strong hollow tubes to be/used as bridges. For example, the tube can be filled with a chitosan solution and bridge the two ends of a cylindrical disconnected bone. The rigid structures are also useful for forming an intervertebral fusion or a spinal prosthesis, e.g., after the removal of a disc, to maintain intervertebral spacing.

A bone can also be replicated in the laboratory using morphometric and biometric information, e.g., obtained from the original bone. Utilizing various imaging techniques such as X-rays, CT and MRI scans, holography, densitometry refraction, etc., the structure, density, configuration, contours, strength, etc. of a particular bone (e.g., a femur head or a metacarpal bone) can be replicated using the compositions and inserted as a functional composition. See, e.g., Zentner et al., 1996, Angle Orthodontist 66:463; Ko, 1998, J. Neurosurg. 88:777; Katz et al, 1998, Med. Eng. & Physics 20:114; Abe et al., 1998, Neurologia Medico-Chirurgica 38:746. Components of articulated structures such as artificial knees or hips could also be constructed using these compositions. These articulated structures can, for example, comprise rigid bone growth-promoting compositions as described herein, cartilage induced, e.g., by the method disclosed in U.S. Pat. No. 5,837,258, and a capsule, e.g., created by chitosan membranes as disclosed in Chandy et al., 1990, Biomat. Art. Cells, Art. Org. 18:1-24 or Rao et al., 1997, J. Biomed. Mat. Res. 34:21-28. Due to the angiogenic, osteoconductive, and osteoinductive nature of the compositions, it would be expected that the artificial bone structures made from those compositions would ultimately be replaced with new host bone.

The composition may also be used at bone fractures to accelerate healing, or at the junctions between native bone and implants such as knee or hip replacements to prevent loosening of the prosthesis. In particular, use of the compositions on fractures (e.g. of the vertebra, hip, or wrist) may be indicated for patients with osteoporosis, since the angiogenic and osteogenic properties of the compositions would be expected to strengthen osteoporotic bone advantageously.

The composition may be used as a prophylactic treatment to prevent fractures in patients with osteoporosis. Many osteoporotic bones are poor in hematogenous tissue also. Many osteoporotic patients have chronic forms of anemia. In this embodiment, bones that are at risk for fracture in osteoporotic patients are first identified by measuring bone density. Bone density is measured using MRI, X-ray, CT-scan, duplex ultrasound or any other imaging system known in the art for that purpose. The degree of risk for fracture is then assessed based on the bone density measurement. The bones with the highest risk for fracture are then treated with a composition of the present invention by injecting the composition directly into the bone at the points where risk for fracture is highest. A preferred apparatus for performing these injections is that disclosed in Provisional Patent Application Ser. No. 60/132,852 the disclosure of which is herein incorporated by reference in its entirety. Since the composition must flow through a cannula and into the bone, the composition to be injected must be thinner than compositions that are applied directly to bone defects.

Various formulations of the composition may be prepared. An example of a useful composition formulation for this invention is a composition where erythropoietin as the hemopoietic agent is present at 1-50,000 units, or 0.1 to 1% of volume; hyaluronic acid as the angiogenic agent is present at 10% to 50% of volume; the bone molecular signaling material is a combination of demineralized growth factor (DBM) present at 5-40% by volume of the composition and non-decalcified bone matrix (NBM) present at 5-30% by volume of the composition; the scaffolding material is cancellous bone milled to 0.1-1.5 mm in its longest diameter and is present at 10-40% by volume; and the gel material is a 0.5%-5% (w/v) concentration of a substance selected from the group consisting of chitins, chitosans, alginates, hyaluronic acids, a mixture of alginates with chitosans, or a mixture of hyaluronic acids and chitosans, or hyaluronates, chitins, chitosans and alginates present at 10-80% by volume. Variations of the formulation may be made according to desired specific function. For example, when the composition is utilized to fill in a large defect, a formulation is utilized which provides a relatively large amount of scaffolding to provide a structure that will support the developing vasculature and bone. An example of such a formulation is (all percentages referring to percent by volume of the composition): cancellous bone, 40%-50%, preferably 40%; DBM, 5-30%, preferably 10%; NBM, 5-30%, preferably 10%; hyaluronic acid 10% to 50%, preferably 30%; erythropoietin 3000 Units or less than 1%. Another example of the composition is cancellous bone, 40-50%, DBM, 5-30%; NBM, 5-30%; hyaluronic acid 10% to 50%; chitosan 0.1% to 20%; and erythropoietin 30,000 Units or less than 2%. An exemplary such formulation is cancellous bone 40%; DBM 10%; NBM 10%; hyaluronic acid 30%; chitosan 5%; and erythropoietin at 30,000 Units.

If the composition is utilized to stimulate bone formation where a supporting scaffolding is not needed, such as at the site of a fracture, or around an allograft or autograft, a minimal amount of scaffolding is utilized, but a relatively large amount of an angiogenic factor or of a combination of angiogenic factors may be advantageous to promote rapid fusion at the fracture or graft-host interface. A relatively large amount of gel-forming material may also be advantageous in this situation to assure minimal movement of the composition. An example of such a formulation is (all percentages referring to percent by volume): cancellous bone, 0.1-30%, preferably 10%; DBM, 5-15%, preferably 10%; NBM, 5-15%, preferably 10%; 10% to 50% hyaluronic acid, preferably 30%; erythropoietin 3000 units or less than 1% of the composition; and a 3-10% (w/v) chitosan gel, present at 20-90% of the composition, preferably a 5% (w/v) gel, present at 40% of the composition.

In another embodiment, the composition can be formulated for the stimulation of myelogenous elements with emphasis on megakaryocytopoiesis, thrombopoiesis and platelet development simultaneously with remodeling bone. In this embodiment the composition includes glycosoaminoglycans (GAG) or proteoglycans with megakaryocytic and thrombopoietic activity. For example, a suitable such formulation is a combination of: one or more of the glycosoaminoglycans (GAG) with megakaryocytic and thrombopoietic activity; one or more angiogenic agents; a material comprising demineralized bone matrix and non-decalcified bone matrix optionally including hyaluronic acid, wherein the demineralized bone matrix is present at 5-50%, and the non-decalcified bone matrix is present at 5-50% of the composition; a scaffolding material comprising cancellous bone, wherein the cancellous bone is milled to 0.1-1.5 mm in its longest diameter and is present at 10-50% of the composition; and a gel material of a 0.5-25% (w/v) concentration present at 10-80% by volume of the composition (wherein all percentages are given as volume percent of the composition). A preferred composition includes, for example, 10% DBM, 10% NBM, 10% scaffold material (e.g. cancellous bone), 50,000 units of one or more hemopoietic factors, 2% GAG's, 18% angiogenic factors, and 50% gel material including, optionally, gel material in the form of vesicles, micelles or the like.

Suitable GAG's for such a formulation include hemopoietic factors, dermatans, dermatan sulfate, heparin and heparans, hyaluronic acid and hyaluronans, chitin and chitosans, and alginates. Suitable angiogenic agents for the formulation are angiogenins, vascular endothelial growth factors, chitin, chitosan, chitosan derivatives and complexes; hyaluronic acid, hyaluronan, hyaluronan derivatives and complexes; alginates alginate derivatives and alginate complexes, and any combination thereof, for example a combination of chitin or chitosan with hyaluronic acid or hyaluronan, or a combination of alginate with hyaluronic acid or a hyaluronan derivative, or a combination of chitin or chitosan with hyaluronic acid or hyaluronan and alginates. The gel material is composed of, for example, chitosan, alginate, hyaluronic acid, a mixture of alginate with chitosan, or a mixture of hyaluronic acid and chitosan.

At least one hemopoietic agent or bone molecular signaling material may be enclosed or encapsulated in carrier material components selected from the group comprising hyaluronates, alginates, chitosans, compositions of chitosans and alginates, chitosans and hyaluronic acids, chitosans, alginates and hyaluronates, free floating or contained in vesicles further developed from combinations of the same various components or form hydrocarbons and/or from surfactants or from a combination of the various components hereof (e.g., vesicles within larger vesicles). For example, carrier vesicles may be formed of chitosans, alginates or hyaluronans and can be configured to carry the one or more hemopoietic agent in the vesicle interior. Additionally, other methods to insure the minimal amount of movement of the composition from the site of application may be used. For example, the topical application of calcium to an alginate excipient causes the composition to remain in place, and reduces the flow properties of the composition. Experimental data demonstrates the retention properties of a composition using an alginate excipient with the addition of calcium after the composition has been localized to the site of the bone defect.

Additionally, a group of co-stimulators of growth and cell survival selected from the group of vitamins A, vitamin B complex, vitamin C, D and E may be added to the composition to stimulate and maintain the cellular and tissue environment necessary for optimal function. When present, such cofactors are present at 3% or less by volume of the composition, but at least 0.1% by volume of the composition.

Furthermore, the composition may contain one or more materials for regulating the pH of the composition selected from the group of acetic acid, ascorbic acid, phosphoric acid, acetylsalicylic acid, hydrochloric acid, nitric acid, phosphates, carbonates, bicarbonates, sulfates. The pH of the composition can be adjusted as known in the art to a value of about 4.0 to about 8.0, preferably from about 6.0 to about 8.0, more preferably less than about 7.4 (but still at least about 6.0), still more preferably less than about 7.0, for example about 6.8, to further promote bone growth. Alternatively, even lower pH values, e.g. from about 4.0 to about 5.0 may be preferred in terms of stimulating tissue regrowth when endovascular tissue is involved.

Additionally, trace minerals such as magnesium, manganese, zinc, cobalt, iron, iodine, selenium, chromium, fluoride, molybdenum, cooper, phosphates, silicon, strontium and others, and salts thereof may also be added in trace amounts to the composition. When included, such trace elements are present at 1% or less by volume of the composition.

Table 1 sets forth the relative contributions of each material in various embodiments of the bone paste as set forth herein. For the table: %: Refers to Weight/Volume=W/V or to Weight/Weight=W/W or to Volume/Weight=V/W; COMP: Composition; EPO: hemopoietic (erythropoietic) agents; ANGIO: angiogenic agents; SIGMOL: bone molecular signaling agents; SCAFF: scaffolding materials; GEL: gel forming substances and carriers; VES: vesicles, cysts or micelles or substances producing these carrier structures; pH: one or more substances used to adjust the pH or acid/base balance of the composition; and COFAC: One or more substances that are cofactors or environmental modulators of the active agents.

The following table is included to demonstrate preferred embodiments of the invention. It should be appreciated by those of skill in the art that many changes can be made in the specific embodiments that are disclosed and still obtain a like or similar result without departing from the spirit and scope of the invention, therefore all matter set forth is to be interpreted as illustrative and not in a limiting sense.

TABLE 1

| COMP | EPO | ANGIO | SIG-MOL | SCAFF | GEL | YES | pH | CO-FAC |
|---|---|---|---|---|---|---|---|---|
| 1 | ≤1% | ≤1% | ≤10% | ≤50% | ≤50% | NO | YES | YES |
| 2 | ≤1% | ≤1% | ≤10% | ≤50% | ≤50% | YES | YES | YES |
| 3 | ≤1% | ≤1% | ≤30% | ≤50% | ≤50% | NO | YES | YES |
| 4 | ≤1% | ≤1% | ≤30% | ≤50% | ≤50% | YES | YES | YES |
| 5 | ≤1% | ≤1% | ≤60% | ≤50% | ≤50% | NO | YES | YES |
| 6 | ≤1% | ≤1% | ≤60% | ≤50% | ≤50% | YES | YES | YES |
| 7 | ≤1% | ≤1% | ≤30% | ≤30% | ≤50% | NO | YES | YES |
| 8 | ≤1% | ≤1% | ≤30% | ≤30% | ≤50% | YES | YES | YES |
| 9 | ≤1% | ≤1% | ≤30% | ≤50% | ≤30% | NO | YES | YES |
| 10 | ≤1% | ≤1% | ≤30% | ≤50% | ≤30% | YES | YES | YES |
| 11 | ≤1% | ≤1% | ≤60% | ≤30% | ≤30% | NO | YES | YES |
| 12 | ≤1% | ≤1% | ≤60% | ≤30% | ≤30% | YES | YES | YES |
| 13 | ≤1% | ≤1% | ≤30% | ≤80% | ≤10% | NO | YES | YES |
| 14 | ≤1% | ≤1% | ≤30% | ≤80% | ≤10% | YES | YES | YES |
| 15 | ≤3% | ≤1% | ≤10% | ≤50% | ≤50% | NO | YES | YES |
| 16 | ≤3% | ≤1% | ≤10% | ≤50% | ≤50% | YES | YES | YES |
| 17 | ≤3% | ≤1% | ≤30% | ≤50% | ≤50% | NO | YES | YES |
| 18 | ≤3% | ≤1% | ≤30% | ≤50% | ≤50% | YES | YES | YES |
| 19 | <3% | <1% | <60% | <50% | <50% | NO | YES | YES |
| 20 | <3% | <1% | <60% | <50% | <50% | YES | YES | YES |
| 21 | <3% | <1% | <30% | <30% | <50% | NO | YES | YES |
| 22 | <3% | <1% | <30% | <30% | <50% | YES | YES | YES |
| 23 | <3% | <1% | <30% | <50% | <30% | NO | YES | YES |
| 24 | <3% | <1% | <30% | <50% | <30% | YES | YES | YES |
| 25 | <3% | <1% | <60% | <30% | <30% | NO | YES | YES |
| 26 | <3% | <1% | <60% | <30% | <30% | YES | YES | YES |
| 27 | <3% | <1% | <30% | <80% | <10% | NO | YES | YES |
| 28 | <3% | <1% | <30% | <80% | <10% | YES | YES | YES |
| 29 | <3% | <3% | <10% | <50% | <50% | NO | YES | YES |
| 30 | <3% | <3% | <10% | <50% | <50% | YES | YES | YES |
| 31 | <3% | <3% | <30% | <50% | <50% | NO | YES | YES |
| 32 | <3% | <3% | <30% | <50% | <50% | YES | YES | YES |
| 33 | <3% | <3% | <60% | <50% | <50% | NO | YES | YES |
| 34 | <3% | <3% | <60% | <50% | <50% | YES | YES | YES |
| 35 | <3% | <3% | <30% | <30% | <50% | NO | YES | YES |
| 36 | <3% | <3% | <30% | <30% | <50% | YES | YES | YES |
| 37 | <3% | <3% | <30% | <50% | <30% | NO | YES | YES |
| 38 | <3% | <3% | <30% | <50% | <30% | YES | YES | YES |
| 39 | <3% | <3% | <60% | <30% | <30% | NO | YES | YES |
| 40 | <3% | <3% | <60% | <30% | <30% | YES | YES | YES |
| 41 | <3% | <3% | <30% | <80% | <10% | NO | YES | YES |
| 42 | <3% | <3% | <30% | <80% | <10% | YES | YES | YES |
| 43 | <1% | <3% | <10% | <50% | <50% | NO | YES | YES |
| 44 | <1% | <3% | <10% | <50% | <50% | YES | YES | YES |
| 45 | <1% | <3% | <30% | <50% | <50% | NO | YES | YES |
| 46 | <1% | <3% | <30% | <50% | <50% | YES | YES | YES |
| 47 | <1% | <3% | <60% | <50% | <50% | NO | YES | YES |
| 48 | <1% | <3% | <60% | <50% | <50% | YES | YES | YES |
| 49 | <1% | <3% | <30% | <30% | <50% | NO | YES | YES |
| 50 | <1% | <3% | <30% | <30% | <50% | YES | YES | YES |
| 51 | <1% | <3% | <30% | <50% | <30% | NO | YES | YES |
| 52 | <1% | <3% | <30% | <50% | <30% | YES | YES | YES |
| 53 | <1% | <3% | <60% | <30% | <30% | NO | YES | YES |
| 54 | <1% | <3% | <60% | <30% | <30% | YES | YES | YES |
| 55 | <1% | <3% | <30% | <80% | <10% | NO | YES | YES |
| 56 | <1% | <3% | <30% | <80% | <10% | YES | YES | YES |

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which modifications do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

What is claimed is:

1. A method for generating bone in a patient, comprising: implanting in the patient a composition comprising;
   erythropoietin;
   at least one angiogenic agent;
   a bone molecular signaling material;
   a scaffolding material comprising cancellous bone;
   a gel component; and
   a carrier encapsulating the erythropoietin.

2. The method of claim 1 wherein said gel component is present at 10-80% by volume of the composition.

3. The method of claim 1 wherein said gel component comprises a 0.5-25% (w/v) concentration of a material selected from the group consisting of: chitin, chitosan, alginate, hyaluronic acid, and any combination thereof, wherein the gel component is present at 10-80% by volume of the composition.

4. The method of claim 1 wherein the bone molecular signaling material is selected from the group consisting of: demineralized bone matrix, non-decalcified bone matrix, and a combination thereof.

5. The method of claim 3 wherein the bone molecular signaling material comprises demineralized bone matrix and non-decalcified bone matrix and optionally hyaluronic acid, wherein said demineralized bone matrix is present at 5-50% by volume, and said non-decalcified bone matrix is present at 5-50% by volume of the composition.

6. The method of claim 5 wherein hyaluronic acid is present at 5-30% by volume of the composition.

7. The method of claim 1 wherein the composition also includes at least one member selected from erythropoietin growth factors and hematogenous-stimulating factors.

8. The method of claim 1 wherein the at least one angiogenic agent is selected from the group consisting of: angiogenins, vascular endothelial growth factors, chitins, chitosans, chitin derivatives and complexes, chitosan derivatives and complexes; hyaluronic acids, hyaluronans, hyaluronan derivatives, hyaluronan complexes; alginates alginate derivatives, alginate complexes, and any combination thereof.

9. The method of claim 1 wherein the scaffolding material comprises cancellous bone milled to about 0.1-1.5 mm in its longest diameter and present at 10-50% by volume of the composition.

10. The method of claim 1 wherein the encapsulating carrier comprises a carrier structure selected from the group consisting of vesicles and micelles, the carrier structure formed of a compound selected from the group consisting of: hyaluronic acid, hyaluronates, alginates, chitosans, hydrocarbons, surfactants or any combination thereof.

11. A method of generating bone in a patient, comprising: implanting in the patient a bone paste composition comprising
   a. one or more hemopoietic agents selected from a group consisting of: erythropoietin, erythropoietin growth factors, and hemopoietic factors, present in an amount from 10 to 50,000 U or 3% or less by volume of the composition;

b. one or more angiogenic agents comprising hyaluronic acid components comprising a mixture of sulfated and non-sulfated hyaluronic acid components;
c. a bone molecular signaling material comprising demineralized bone matrix and non-decalcified bone matrix optionally in combination with hyaluronic acid, wherein said demineralized bone matrix is present at 5-50% by volume of the composition, and said non-decalcified bone matrix is present at 5-50% by volume of the composition, wherein when present hyaluronic acid is present at 5 to 20% of the composition;
d. a scaffolding material comprising cancellous bone, wherein said cancellous bone is milled to 0.1-1.5 mm in its longest diameter and is present at 10-50% by volume of the composition; and
e. a gel material comprising a 0.5-25% (w/v) concentration of a compound selected from the group consisting of chitosans, alginates, hyaluronic acids, and any combination thereof.

12. The method of claim 11 wherein the one or more angiogenic agents also comprise chitosan components selected from the group consisting of chitosans, chitosan derivatives, and chitosan complexes.

13. The method of claim 11 wherein the gel material is present at 10-30% by volume of the composition.

14. A method for generating bone in a patient, comprising: implanting in the patient a composition comprising;
at least one hemopoietic agent, the at least one hemopoietic agent including erythropoietin;
at least one angiogenic agent comprising a mixture of sulfated and non-sulfated hyaluronic acid components;
at least one bone molecular signaling material;
at least one scaffolding material; and
at least one carrier substance.

15. The method of claim 14, wherein the at least one bone molecular signaling material includes an osteoinductive compound.

16. The method of claim 15, wherein the osteoinductive compound is a bone morphogenic protein.

17. The method of claim 14, wherein the at least one carrier substance includes a gel.

* * * * *